United States Patent
Gourlay (10) Patent No.: US 9,636,446 B2
(45) Date of Patent: May 2, 2017

(54) FLUID PROCESSING DEVICE (75) Inventor: Terence Gourlay, Glasgow (GB)

(73) Assignee: University of Strathclyde, Glasgow (GB)

( * ) Notice: Subject to any disclaimer, the term of this patent is extended or adjusted under 35 U.S.C. 154(b) by 498 days.

(21) Appl. No.: 12/993,320

(22) PCT Filed: May 18, 2009

(86) PCT No.: PCT/GB2009/001233
§ 371 (c)(1),
(2), (4) Date: Feb. 1, 2011

(87) PCT Pub. No.: WO2009/141589
PCT Pub. Date: Nov. 26, 2009

(65) Prior Publication Data
US 2011/0297615 A1 Dec. 8, 2011

(30) Foreign Application Priority Data

May 20, 2008 (GB) .................................. 0809092.0

(51) Int. Cl.
*B01D 15/08* (2006.01)
*B01D 15/00* (2006.01)
*A61M 1/34* (2006.01)
*A61M 1/36* (2006.01)

(52) U.S. Cl.
CPC ........ *A61M 1/3472* (2013.01); *A61M 1/3475* (2014.02); *A61M 1/3679* (2013.01)

(58) Field of Classification Search
CPC . A61M 1/3472; A61M 1/3475; A61M 1/3679
USPC ................................................ 210/435, 660
See application file for complete search history.

(56) References Cited

U.S. PATENT DOCUMENTS

| 3,485,751 A | 12/1969 | Herrmann |
| 3,742,946 A | 7/1973 | Grossman |
| 4,183,811 A * | 1/1980 | Walch ............... A61M 1/3472 210/321.83 |

(Continued)

FOREIGN PATENT DOCUMENTS

| EP | 0070738 A1 | 1/1983 |
| EP | 0953361 A1 | 11/1999 |

(Continued)

OTHER PUBLICATIONS

PCT International Search Report for PCT/GB2009/001233 (Oct. 20, 2009).

*Primary Examiner* — Dirk Bass
(74) *Attorney, Agent, or Firm* — LeClairRyan, a Professional Corporation (57) ABSTRACT

The present invention relates to a system, apparatus, and method for separating components of a fluid, e.g. blood, which eliminates the need for expensive hardware and produces a stabilized waste product. The system comprises an apparatus or device (V) for separating components of a fluid (15') comprising a container (5') having at least one separation or filtration member (10') capable of selectively separating or filtering at least one component from the fluid, and a superabsorbent material (20') capable of absorbing the at least one component separated from the fluid, and thereby providing a processed fluid free or substantially free of said at least one component; and agitation means.

21 Claims, 4 Drawing Sheets (56) References Cited

U.S. PATENT DOCUMENTS

| | | | |
|---|---|---|---|
| 4,206,050 A | | 6/1980 | Lammers et al. |
| 4,631,050 A | | 12/1986 | Reed et al. |
| 4,898,572 A | | 2/1990 | Surugue nee Lasnier et al. |
| 4,966,758 A | | 10/1990 | Belt |
| 5,045,207 A | * | 9/1991 | Fecondini .............. B01D 61/18 210/321.75 |
| 5,211,850 A | | 5/1993 | Shettigar et al. |
| 5,858,238 A | * | 1/1999 | McRea et al. ................ 210/645 |
| 5,876,611 A | | 3/1999 | Shettigar |
| 6,153,104 A | | 11/2000 | Robertson |
| 6,221,264 B1 | | 4/2001 | Ishida et al. |
| 7,794,420 B2 | | 9/2010 | Perovitch et al. |
| 8,187,465 B2 | | 5/2012 | Nierich |
| 2004/0007540 A1 | | 1/2004 | Verpoort et al. |
| 2004/0081588 A1 | | 4/2004 | Hammerstedt et al. |
| 2004/0251195 A1 | | 12/2004 | Oka et al. |
| 2005/0133439 A1 | | 6/2005 | Blickhan |
| 2005/0133447 A1 | | 6/2005 | Tsai et al. |
| 2005/0186183 A1 | * | 8/2005 | DeAngelo ................ A01N 1/02 424/93.7 |
| 2006/0054557 A1 | | 3/2006 | Hori et al. |
| 2006/0175242 A1 | | 8/2006 | Dorian |

FOREIGN PATENT DOCUMENTS

| | | | |
|---|---|---|---|
| EP | 1579838 | A1 | 9/2005 |
| FR | 2821762 | A1 | 9/2002 |
| WO | 9301858 | A1 | 2/1993 |
| WO | 9819722 | A1 | 5/1998 |
| WO | 0224256 | A1 | 3/2002 |
| WO | 2006062808 | A2 | 6/2006 |

\* cited by examiner

FLUID PROCESSING DEVICE

This is a national stage application under 35 U.S.C. §371 of PCT/GB2009/001233, filed May 18, 2009, which claims priority to GB 0809092.0, filed May 20, 2008.

FIELD OF INVENTION

The present invention relates to a device for processing a fluid, and in particular, though not exclusively, to a passive cell separation device for use in processing blood, for example, in a surgical environment.

BACKGROUND TO INVENTION

Blood recovery in the surgical environment or during trauma can be performed by a variety of processes. Blood lost from a surgical site is commonly required to be processed into a cell concentrate prior to readministration. With blood being generally in short supply and increasingly becoming a rechargeable commodity, there is an increasing interest in recovering blood that would have traditionally been lost to surgical drainage.

The recovery of blood commonly requires a suction system and a centrifuge device to concentrate the blood, which necessitates the purchase and maintenance of expensive and cumbersome equipment.

Additionally, the current concern in both the medical and public sectors regarding hospital or blood-borne infections has triggered a greater interest in auto-transfusion during surgical procedures.

Typically, in the case of post-cardiac surgery, there is a need to concentrate the blood of a haemodeficient patient from a concentration of approximately 22% packed cell volume to about 70 to 80% packed cell volume.

It is an object of at least one embodiment of at least one aspect of the present invention to seek to obviate or at least mitigate one or more disadvantages in the prior art.

It is an object of at least one embodiment of at least one aspect of the present invention to provide a convenient single use disposible device for processing blood, suitable for flat-pack storage, and which eliminates the need for expensive hardware.

It is an object of at least one embodiment of at least one aspect of the present invention to provide a blood-processing device which produces a stabilised waste product.

It is an object of at least one embodiment of at least one aspect of the present invention to provide a device for processing blood into a concentrate comprising cellular components. This may be particularly useful in third world or military field environments where access to expensive centrifugal processing technologies is restricted, but there remains a significant need for processed donor blood products.

It is an object of at least one embodiment of at least one aspect of the present invention to provide a system comprising a blood-processing device; and agitation means, e.g. an orbital shaker, for improving the efficiency of the blood-processing device.

It is an object of at least one embodiment of at least one aspect of the present invention to provide a method of concentrating blood or removing specific blood components comprising separating or filtering at least one component from the fluid through at least one separation or filtration member, wherein the at least one component separated or filtered from the fluid may be permanently removed or retained by a superabsorbent material.

It is an object of at least one embodiment of at least one aspect of the present invention to provide a use of a superabsorbent material for separating or removing at least one component from a fluid such as blood.

SUMMARY OF INVENTION

According to a first aspect of the present invention there is provided an apparatus or device for separating components of a fluid comprising a container having at least one separation or filtration member capable of selectively separating or filtering at least one component from the fluid, and a superabsorbent material capable of absorbing the at least one component separated from the fluid, and thereby providing a processed fluid free or substantially free of the said at least one component. It is to be understood that the filtration member and the superabsorbent material may be unitary in nature or formed from two or more components.

Conveniently, the separation device may be capable of reducing the volume of the fluid-to-be-processed by at least 20%, preferably at least 30%, more preferably at least 40%, and typically approximately 50-80%.

Typically, the filtration member and the superabsorbent material may form two separate components.

The container may comprise an inlet, first opening or first aperture, typically near a top portion thereof for introducing the fluid into the container.

The inlet, first opening or first aperture may be in communication with a receiving portion, compartment or cavity located inside the device and into which the fluid to be processed is initially received, prior to the separation/filtration step.

In use, a fluid may be provided into the receiving portion of the device through the inlet, first opening or first aperture.

The inlet, first opening or first aperture may be further equipped with means for feeding a fluid into the device, e.g. tubing.

The inlet, first opening or first aperture may be equipped with a flow control system, e.g. a valve or a seal, to prevent fluid from escaping from the receiving portion, compartment or cavity.

The volume and shape of the receiving portion, compartment or cavity may be at least partially defined by said at least one separation or filtration member.

Said at least one separation or filtration member may be a rigid and/or self-supported member.

Alternatively, said member may be flexible and/or supported by a non-reactive supporting material, e.g. a perforated plastic material.

The member may comprise a first side facing toward the receiving portion, compartment or cavity and a second side facing in the opposite direction.

In use, a fluid fed into the receiving portion, compartment or cavity of the device comes into contact with a first side of said at least one separation or filtration member.

Typically, the superabsorbent material may be in contact with or adjacent the second side face of said member.

Conveniently, the second side face of the member may be in contact with a support material impregnated with the superabsorbent material.

The superabsorbent material may be located between the second side face of the member and an inside wall of the container. In such an arrangement, in use, the at least one component selectively separated or filtered from the fluid may migrate outwardly, with respect to the wall of the container, from the receiving portion, compartment or cavity towards the superabsorbent material.

The device may comprise a substantially hollow portion between the superabsorbent material and the inside wall of the container. By such provision the impregnated material may be allowed to expand upon absorption of the at least one filtered component.

Alternatively, the receiving portion, compartment or cavity may be provided between an inside wall of the container and a first side face of the at least one separation or filtration member. In such an arrangement, in use, the at least one component selectively separated or filtered from the fluid may migrate inwardly, with respect to the wall of the container, from the receiving portion, compartment or cavity towards the superabsorbent material.

Preferably, the superabsorbent material may be provided or enclosed within a volume defined by the second side face of the at least one separation or filtration member. By such provision the at least one separation or filtration member and the superabsorbent material may define a pad-like assembly provided inside the container.

In such an arrangement, the device may further comprise a substantially hollow portion inside the volume defined by the second side face of the at least one separation or filtration member. By such provision the impregnated material may be allowed to expand or swell upon absorption of the at least one filtered component.

Advantageously, the separation or filtration member may be attached to e.g., an inside wall of the container.

In use, absorption by the superabsorbent material "draws" a portion of fluid comprising the at least one component through the separation or filtration member whilst other components are retained in the receiving portion, compartment or cavity. By such provision the apparatus does not require application of any external force to separate the at least one component from the initial fluid. It will be appreciated that the at least one component of the fluid may simply be a portion of the fluid lacking or substantially lacking any solid or particulate material. In this manner, removal of a portion of the fluid will serve to concentrate solid or particulate material, such as proteins, cells, and the like, in the case of blood, in the processed fluid. However, the at least one component will generally comprise a portion of any solid or particulate material formed in the fluid.

The receiving portion, compartment or cavity may be in communication with an outlet, second opening or second aperture, typically near a bottom portion of the container, for removal of said processed fluid.

The outlet, second opening or second aperture may be further equipped with means for retrieving or recovering a processed fluid from the device, e.g. tubing.

The outlet, second opening or second aperture may be equipped with a flow control system, e.g. a valve or a seal.

In use, a processed fluid may be retrieved or recovered from the receiving portion, compartment or cavity of the device through the outlet, second opening or second aperture.

Alternatively, a processed fluid may be retrieved or recovered from the receiving portion, compartment or cavity of the device through the inlet, first opening or first aperture, e.g. by inverting the device.

Conveniently, the container may be in the form of a flexible bag or pouch. By such provision the device may be suitable for flat pack storage.

The bag may be made from a polymeric material, e.g. medical grade polyvinyl chloride (PVC) or a polyolefin material.

Alternatively, the container may be rigid, e.g. in the form of a rigid cylinder. In such instance the container may be made from e.g. medical grade polycarbonate.

Typically, the container may be substantially cylindrical.

Conveniently, the container may comprise a substantially transparent portion, e.g. a transparent vertical strip. By such provision the inside of the receiving portion, compartment or cavity of the device may be visible by a user.

The substantially transparent portion of the container may be provided with measuring means to indicate the level or volume of fluid present inside the receiving portion, compartment or cavity of the device. By such provision, after filling the device with a desired quantity of fluid, a user may be able to determine when a sufficient amount of the component-to-be-removed has been absorbed by the superabsorbent material.

The at least one separation or filtration member may be a membrane, e.g. a semi-permeable membrane.

Preferably, the membrane may be a porous filtration membrane.

The membrane may be made from a polyolefin material, e.g. polypropylene, or another polymeric material such as nylon or polyethersulfone.

The permeability of the membrane may be chosen according to the type of fluid to be processed and/or the specific components to be separated or removed from the fluid.

Typically, permeability may be determined by selecting a specific pore size for the membrane.

In use, when processing blood, an effective membrane pore size of 0.2 µm, for example, may allow water, small salts and proteins to pass through the membrane and be removed from the blood. Alternatively, an effective membrane pore size of 5 to 8 µm, for example, may also allow platelets and larger proteins to pass through the membrane. Thus, it is possible to concentrate the cellular components of blood.

The superabsorbent material may be made from a superabsorbent polymer, e.g. a polyacrylate or a polyacrylamide.

Preferably, the superabsorbent material may be made from sodium polyacrylate.

Conveniently, the superabsorbent material may be in powder form.

In use, the superabsorbent material may form a stable gel upon absorption of a fluid, e.g. water.

The at least one component separated from a fluid may be permanently removed from the fluid and/or retained by the superabsorbent.

The support material impregnated with the superabsorbent material may comprise a cellulosic material or a polyester material, e.g. a cellulose tissue material or a polyester fibre material.

The superabsorbent material and/or the support material may further comprise additives.

Conveniently, the superabsorbent material and/or the support material may be impregnated with stabilising agents, e.g. anti-microbial agents, to further stabilise the waste product for safe disposal.

Typically, the device may be a bodily fluid separation device, e.g. a blood separation device. By such provision specific blood components may be removed or separated, and the processed blood may be further processed, e.g. readministered into a patient.

The device may be further equipped with further processing means, e.g. a leukocyte depleting filter which may be connected to the outlet, second opening or second aperture of the device.

In use, the device may be used in a surgical environment.

In use, the device may be attachable to a static piece of surgical equipment, e.g. a stand or a bed.

In use, the device may be attached to agitation means, e.g. vibrating means or shaking means such as an orbital shaker, in order to improve the efficiency of the separation device.

According to a second aspect of the present invention there is provided a system comprising an apparatus or device for separating components of a fluid; and agitation means. By such provision the efficiency of the fluid-processing device may be enhanced.

Preferably, the apparatus or device may be a separation device according to the present invention as described herein above.

Typically, the agitation means may comprise e.g. vibrating means or shaking means.

Preferably, the agitation means may comprise an orbital shaker.

Conveniently, the agitation means may be adapted for agitating the separation device.

Typically, the agitation means may be provided with a receiving portion for receiving the separation device.

Typically, the receiving portion may comprise a receiving surface for receiving the separation device.

In use, the receiving surface may be substantially horizontal.

Typically also, the receiving portion may be provided with a raised portion, e.g. a substantially vertically-extending portion, around its periphery for maintaining the separation device on the receiving surface.

Conveniently, the agitation means may be provided with attaching means for securing the separation device to the receiving portion.

Advantageously, the agitation means may be further provided with a closably openable and substantially rigid covering portion, e.g. a lid, for protecting the separation device. By such provision, in use, the separation device may be protected from accidental damage and/or contamination.

Conveniently, the agitation means may be operated by mains power supply, battery pack, or manually.

Typically, the separation device or apparatus may be a bodily fluid separation device, e.g. a blood separation device.

According to a third aspect of the present invention there is provided a method for processing a fluid comprising separating or filtering at least one component from the fluid using at least one separation or filtration member, and retaining or removing said at least one separated or filtered component by a superabsorbent material.

The method may comprise a preliminary step consisting of providing a fluid into a separation device.

The method may comprise a final step consisting of retrieving or recovering a processed fluid from the separation device.

The method may be driven by the combined action of gravity and absorption of the at least one component by the superabsorbent material after passing through the separation or filtration member. Absorption by the superabsorbent material "draws" the at least one component through the separation or filtration member.

By such provision the method does not require the application of an external force to separate the at least one component from the fluid.

The fluid may be provided into a receiving portion, compartment or cavity of the device via an inlet, first opening or first aperture near a top portion thereof.

The fluid may be provided into the receiving portion via feeding means, e.g. tubing, which may be connected to the inlet, first opening or first aperture.

The fluid may be fed at a rate controlled by a flow control system, e.g. a valve or a seal, thereby preventing fluid from escaping from the top of the receiving portion.

The processed fluid may be retrieved or recovered from the receiving portion, compartment or cavity of the device via an outlet, second opening or second aperture near a bottom portion of the device.

The processed fluid may be retrieved or recovered at a rate controlled by a flow control system, e.g. a valve or a seal, connected with the outlet, second opening or second aperture.

Alternatively, the processed fluid may be retrieved or recovered from the receiving portion of the device through the inlet, first opening or first aperture, e.g. by inverting the device.

The method may comprise continuously providing a fluid inside the device via an inlet, first opening or first aperture, and continuously retrieving the processed fluid via an outlet, second opening or second aperture. By such provision the level of fluid inside the device may be maintained at a substantially constant level.

Conveniently, the method may comprise providing a fluid into the separation device according the present invention as described herein above.

The method may comprise the superabsorbent permanently removing and/or retaining the at least one component separated from the fluid.

The method may comprise agitating the device during processing of the fluid. By such provision the rate at which the fluid is processed may be increased.

The method may comprise further processing the processed fluid, e.g. removing at least one further component from the processed fluid, e.g. removing leukocytes from processed blood by further processing it through using e.g. a leukocyte-depleting filter.

The method may further comprise disposing of the separation device upon retrieval or recovery of the processed fluid.

Typically, the method comprises processing a bodily fluid, e.g. blood. By such provision specific blood components may be removed or separated, and the processed blood may be further processed, e.g. readministered into a patient.

In use, a subject's bodily fluid may be provided into the receiving portion of the separation device while the device is provided on or attached to a static piece of surgical equipment such as a stand or a bed. When a desired amount of bodily fluid is provided in the separation device, the inlet may be closed to prevent leakage, and the device transferred to agitation means to improve separation efficiency.

Alternatively, the separation device may be provided on or in said agitation means prior to its receiving portion being filled with a subject's bodily fluid. By such provision agitation may be applied either simultaneous or subsequent to a subject's bodily fluid being provided into the receiving portion of the device.

According to a fourth aspect of the present invention there is provided a use of a superabsorbent material for separating or removing at least one component from a bodily fluid, e.g. blood.

The superabsorbent material may be made from a superabsorbent polymer, e.g. a polyacrylate.

Conveniently, the superabsorbent material may be in powder form.

In use, the superabsorbent material may form a stable gel upon absorption of a fluid, e.g. water.

The at least one component separated from a fluid may be permanently removed from the fluid and/or retained by the superabsorbent.

The superabsorbent material may be impregnated into a support material.

The support material impregnated with the superabsorbent material may comprise a cellulosic material or a polyester material, e.g. a cellulose tissue material or a polyester fibre material.

The superabsorbent material and/or the support material may further comprise additives.

Conveniently, the superabsorbent material and/or the support material may be impregnated with stabilising agents, e.g. anti-microbial agents, to further stabilise the waste product for safe disposal.

BRIEF DESCRIPTION OF DRAWINGS

Embodiments of the invention will now be given by way of example only, and with reference to the accompanying drawings, which are.

DETAILED DESCRIPTION OF DRAWINGS

Figures 1A, 1B:
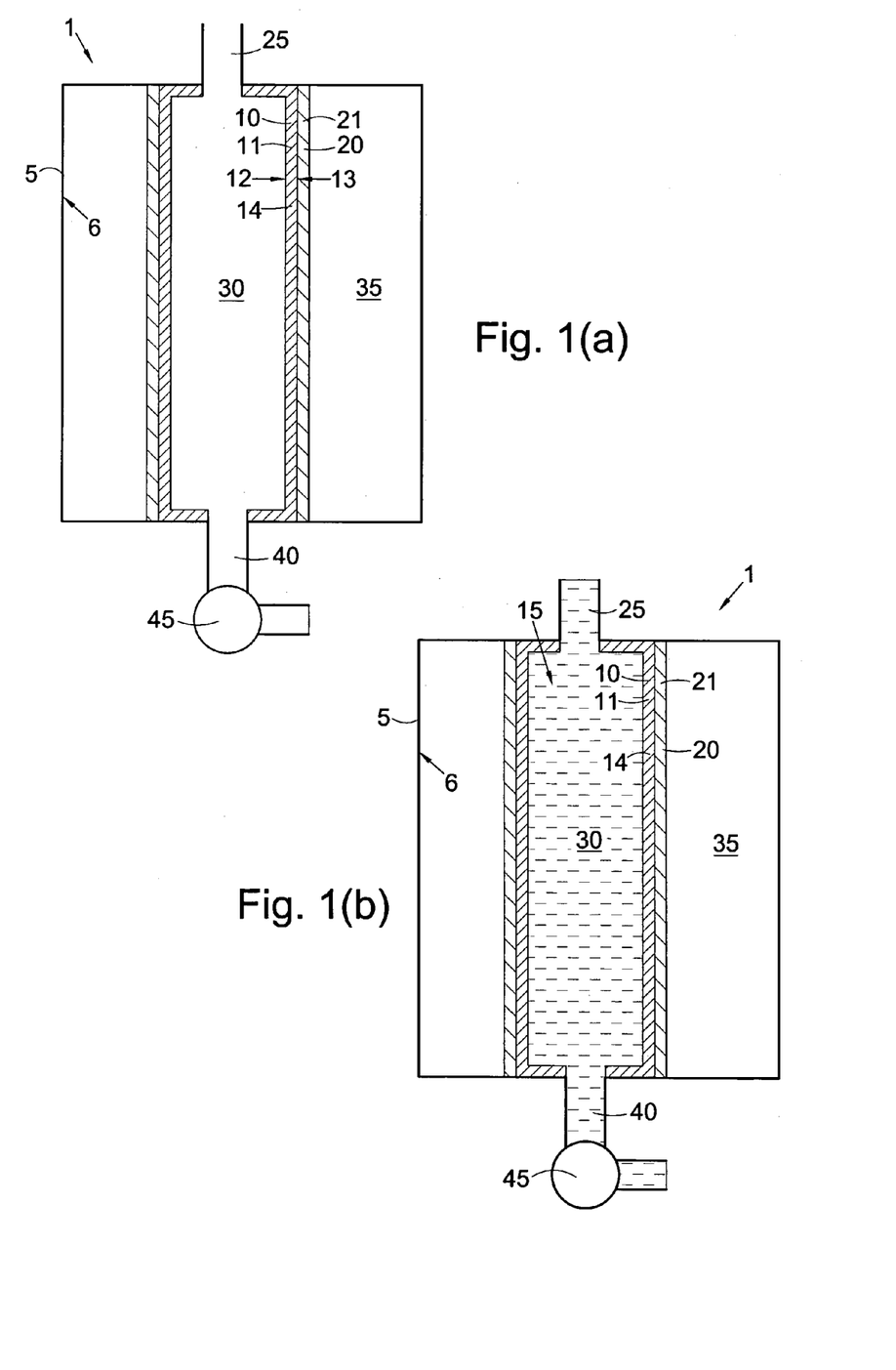
FIG. 1(a) a cross-sectional view of a separation device according to a first embodiment of the present invention.
FIG. 1(b) a cross-sectional view of the separation device of FIG. 1(a), the receiving portion of which is filled with a fluid to be processed.
Figures 1C, 2A:
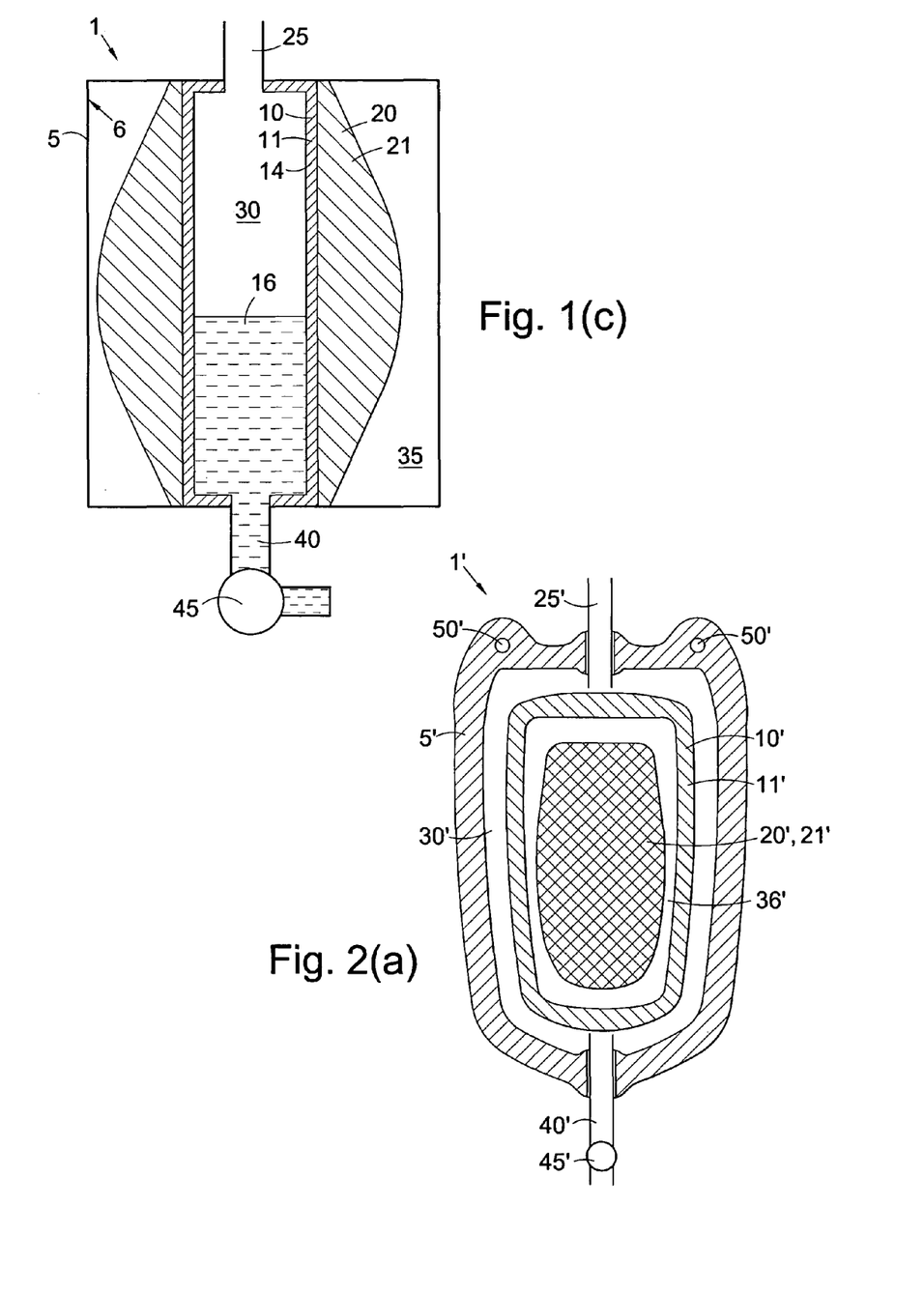
FIG. 1(c) a cross-sectional view of the separation device of FIG. 1(a) at or near the final stage of the separation process.
FIG. 2(a) a cross-sectional front view of a separation device according to a second embodiment of the present invention.

Referring to FIGS. 1(a), 1(b) and 1(c) there is shown an apparatus or device for separating components of a fluid, generally designated 1, according to a first embodiment of the present invention. The separation device 1 comprises a container 5 which contains at least one separation or filtration member 10 capable of separating or filtering at least one component from the fluid 15, and a superabsorbent material 20 capable of removing the at least one component filtered through or separated by the member 10 disposed therein.

Conveniently, the separation device is capable of reducing the volume of the fluid-to-be-processed by at least 20%, preferably at least 30%, more preferably at least 40%, and typically approximately 50-80%.

In this embodiment, the filtration member 10 and the superabsorbent material 20 form two separate components.

The container 5 comprises an inlet, first opening or first aperture 25, typically near a top portion thereof for introducing the fluid 15 into the container 5.

The inlet, first opening or first aperture 25 is in communication with a receiving portion, compartment or cavity 30 located inside the device 1 and into which the fluid 15 to be processed is initially received, prior to the separation/filtration step.

In use, the fluid 15 is provided into the receiving portion, compartment or cavity 30 of the device 1 through the inlet, first opening or first aperture 25.

The volume and shape of the receiving portion, compartment or cavity 30 is at least partially defined by a first separation or filtration member 11.

In this embodiment, the first member 11 is a rigid and/or self-supported member.

The member 11 comprises a first side 12 facing toward the receiving portion, compartment or cavity 30 and a second side 13 facing in the opposite direction.

In use, a fluid 15 fed into the receiving portion, compartment or cavity 30 of the device 1 comes into contact with a first side 12 of the member 11.

The superabsorbent material 20 is in contact with a second side 13 of the member 11.

In this embodiment, the second side 13 of the member 11 is in contact with a support material 21 impregnated with the superabsorbent material 20.

In this embodiment, the superabsorbent material 20 is located between the second side 13 of the member 11 and an inside wall 6 of the container 5. By such provision, in use, the at least one component selectively separated or filtered from the fluid 15 migrates outwardly, with respect to the wall of the container 5, from the receiving portion, compartment or cavity 30 towards the superabsorbent material 20.

In this embodiment, the device 1 comprises a substantially hollow portion 35 between the superabsorbent material 20 and the inside wall 6 of the container 5. By such provision the impregnated material 21 is allowed to expand or swell upon absorption of fluid comprising the at least one filtered component.

In use, absorption by the superabsorbent material 20 "draws" a portion of fluid 15 comprising the at least one component through the separation or filtration member 10 whilst other components are retained in the receiving portion, compartment or cavity 30. By such provision the apparatus 1 does not require application of any external force to separate the at least one component from the fluid 15.

The receiving portion, compartment or cavity 30 is in communication with an outlet, second opening or second aperture 40, typically near a bottom portion of the container 5, for removal of the processed fluid.

The outlet, bottom opening or bottom aperture 40 is further equipped with a flow control system 45, e.g. a valve or a seal.

In use, a processed fluid 16 may be retrieved or recovered from the receiving portion, compartment or cavity 30 of the device through the outlet, second opening or second aperture 40.

Alternatively, the processed fluid 16 may be retrieved or recovered from the receiving portion, compartment or cavity 30 of the device 1 through the inlet, first opening or first aperture 25, e.g. by inverting the device.

In this embodiment, the container 5 is in the form of a rigid cylinder.

The container 5 is made from a polymeric material, e.g. medical grade polyvinyl chloride (PVC).

The container 5 comprises a substantially transparent portion (not shown), e.g. a transparent vertical strip. By such provision the inside of the receiving portion, compartment or cavity 30 of the device 1 is visible by a user during use.

The substantially transparent portion of the container 5 is provided with measuring means to indicate the level or volume of fluid present inside the receiving portion, compartment or cavity 30. By such provision, after filling the device 1 with a desired quantity of fluid 15, a user may be able to determine when a sufficient amount of the component-to-be-removed has been absorbed by the superabsorbent material 20.

The at least one separation or filtration member 10 is a membrane 14, e.g. a semi-permeable porous filtration membrane.

The membrane 14 is made from a polyolefin material, e.g. "Celgard 2500" microporous polypropylene flat sheet membrane (0.2 μm pore size) from Celgard LLC, 13800 South Lakes Dr, Charlotte, N.C. 28273, U.S., or another polymeric material such as nylon or a MicroPES® polyethersulfone hydrophilic flat membrane (Type "4F toa", "5F M", or "6F") from Membrana GmbH, Oehder Straβe 28, D-42289 Wuppertal, Germany.

The permeability of the membrane 14 is chosen according to the type of fluid 15 to be processed and/or the specific components to be separated or removed from the fluid 15.

For example, when using a Celgard 2500 membrane, an effective membrane pore size of 0.2 μm will allow water, small salts and proteins to pass through the membrane.

The superabsorbent material 20 is made from a superabsorbent polymer, e.g. "Super Absorber" (99%+ Cellulose Sodium Polyacrylate superabsorber) from Brightwake Ltd, Lowmoor Business Park, Kirkby-in-Ashfield, Nottinghamshire NG17 7JZ, UK.

In this embodiment, the superabsorbent material 20 is in powder form.

In use, the superabsorbent material 20 forms a stable gel upon absorption of a fluid, e.g. water.

The at least one component separated from a fluid 15 is permanently removed from the fluid 15 and/or retained by the superabsorbent 20.

The support material 21 impregnated with the superabsorbent material 20 comprises a cellulosic material or a polyester material, e.g. a cellulose tissue material or a polyester fibre material.

In this embodiment, the polyacrylate superabsorbent material impregnated in a cellulosic fibrous material is in the form of a Brightwake wound dressing.

The superabsorbent material 20 and/or the support material 21 may further comprise additives.

Conveniently, the superabsorbent material 20 and/or the support material 21 are impregnated with stabilising agents, e.g. anti-microbial agents, to further stabilise the waste product for safe disposal.

In this embodiment, the device 1 is a bodily fluid separation device, e.g. a blood separation device.

Figure 2B:
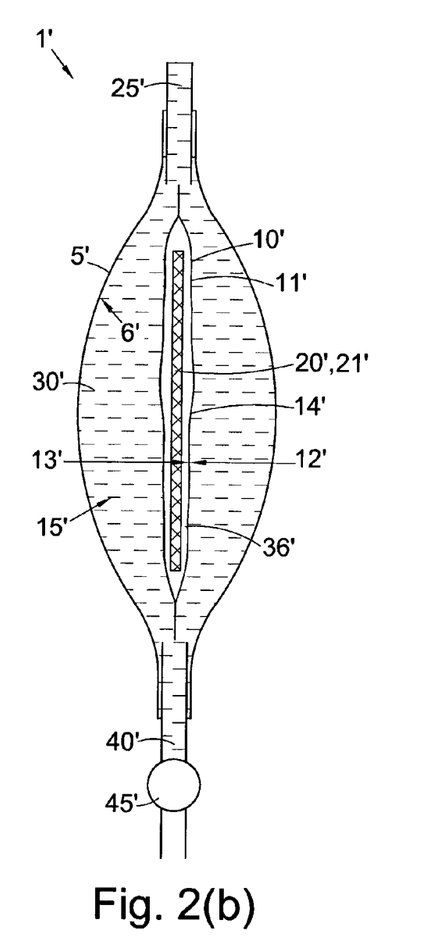
FIG. 2(b) a cross-sectional side view of the separation device of FIG. 2(a), the receiving portion of which is filled with a fluid to be processed.
Figure 2C:
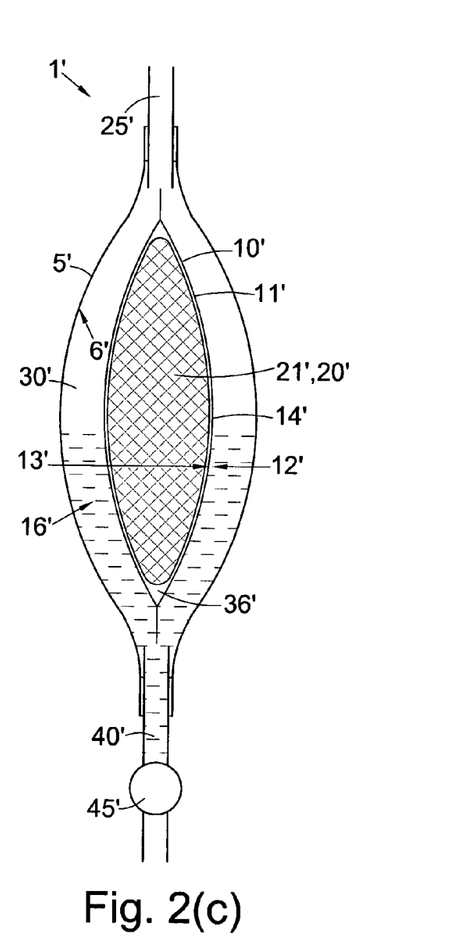
FIG. 2(c) a cross-sectional side view of the separation device of FIG. 2(a); at or near the final stage of the separation process.

Referring now to FIGS. 2(*a*), 2(*b*) and 2(*c*) there is shown an apparatus or device for separating components of a fluid, generally designated 1', according to a second embodiment of the present invention. In this embodiment the container 5' is in the form of a flexible bag or pouch.

The separation device 1' comprises a container 5' which contains at least one separation or filtration member 10' capable of separating or filtering at least one component from a fluid 15', and a superabsorbent material 20' capable of removing the at least one component filtered through or separated by the member 10' disposed therein.

Conveniently, the separation device is capable of reducing the volume of the fluid-to-be-processed by at least 20%, preferably at least 30%, more preferably at least 40%, and typically approximately 50-80%.

In this embodiment, the filtration member 10' and the superabsorbent material 20' form two separate components.

The container 5' comprises an inlet, first opening or first aperture 25', typically near a top portion thereof for introducing the fluid 15' into the container 5'.

The inlet, first opening or first aperture 25' is in communication with a receiving portion, compartment or cavity 30' located inside the device 1' and into which the fluid 15' to be processed is initially received, prior to the separation/filtration step.

In use, the fluid 15' is provided into the receiving portion, compartment or cavity 30' of the device 1' through the inlet, first opening or first aperture 25'.

The volume and shape of the receiving portion, compartment or cavity 30' is at least partially defined by a first separation or filtration member 11'.

In this embodiment, the first member 11' is a self-supported member.

The member 11' comprises a first side 12' facing toward the receiving portion, compartment or cavity 30' and a second side 13' facing in the opposite direction.

In use, a fluid 15' fed into the receiving portion, compartment or cavity 30' of the device 1' comes into contact with a first side 12' of the member 11'.

The superabsorbent material 20' is in contact with or adjacent the second side 13' of the member 11'.

In this embodiment, the second side 13' of the member 11' is in contact with a support material 21' impregnated with the superabsorbent material 20'.

In this embodiment, the receiving portion, compartment or cavity 30' is provided between an inside wall 6' of the container 5' and a first side face of the at least one separation or filtration member 11'. In such an arrangement, in use, the at least one component selectively separated or filtered from the fluid 15' migrates inwardly, with respect to the wall of the container 5', from the receiving portion, compartment or cavity 30' towards the superabsorbent material 20'.

The superabsorbent material 20' is provided or enclosed within a volume defined by the second side face 13' of the at least one separation or filtration member 11'. By such provision the at least one separation or filtration member 11' and the superabsorbent material 20' define a pad-like assembly provided inside the container 5'.

In this embodiment, the member 11' comprises a substantially hollow portion 36' inside the volume defined by the second side face 13' of the member 11'. By such provision the impregnated material 21' is allowed to expand or swell upon absorption of the at least one filtered component.

Advantageously, the separation or filtration member 11' is attached to e.g., an inside wall 6' of the container.

In use, absorption by the superabsorbent material 20' "draws" a portion of fluid 15' comprising the at least one component through the separation or filtration member 10' whilst other components are retained in the receiving portion, compartment or cavity 30'. By such provision the apparatus 1' does not require application of any external force to separate the at least one component from the fluid 15'.

The receiving portion, compartment or cavity 30' is in communication with an outlet, second opening or second aperture 40', typically near a bottom portion of the container 5', for removal of the processed fluid.

The outlet, bottom opening or bottom aperture 40' is further equipped with a flow control system 45', e.g. a valve or a seal.

In use, a processed fluid 16' may be retrieved or recovered from the receiving portion, compartment or cavity 30' of the device through the outlet, second opening or second aperture 40'.

Alternatively, the processed fluid 16' may be retrieved or recovered from the receiving portion, compartment or cavity 30' of the device 1' through the inlet, first opening or first aperture 25', e.g. by inverting the device.

In this embodiment, the container 5' is in the form of a flexible bag or pouch. By such provision the device is suitable for flat pack storage.

The container 5' is made from a polymeric material, e.g. medical grade polyvinyl chloride (PVC).

The container 5' comprises a substantially transparent portion (not shown), e.g. a transparent vertical strip. By such provision the inside of the receiving portion, compartment or cavity 30' of the device 1' is visible by a user during use.

The substantially transparent portion of the container 5' is provided with measuring means to indicate the level or volume of fluid present inside the receiving portion, compartment or cavity 30'. By such provision, after filling the device 1' with a desired quantity of fluid 15', a user may be able to determine when a sufficient amount of the component-to-be-removed has been absorbed by the superabsorbent material 20'.

The at least one separation or filtration member 10' is a membrane 14', e.g. a semi-permeable porous filtration membrane.

The membrane 14' is made from a polyolefin material, e.g. "Celgard 2500" microporous polypropylene flat sheet membrane (0.2 μm pore size) from Celgard LLC, 13800 South Lakes Dr, Charlotte, N.C. 28273, U.S., or another polymeric material such as nylon or a MicroPES® polyethersulfone hydrophilic flat membrane (Type "4F toa", "5F M", or "6F") from Membrana GmbH, Oehder Straße 28, D-42289 Wuppertal, Germany.

The permeability of the membrane 14' is chosen according to the type of fluid 15' to be processed and/or the specific components to be separated or removed from the fluid 15'.

For example, when using a Celgard 2500 membrane, an effective membrane pore size of 0.2 μm will allow water, small salts and proteins to pass through the membrane.

The superabsorbent material 20 is made from a superabsorbent polymer, e.g. "Super Absorber" (99%+ Cellulose Sodium Polyacrylate superabsorber) from Brightwake Ltd, Lowmoor Business Park, Kirkby-in-Ashfield, Nottinghamshire NG17 7JZ, UK.

In this embodiment, the superabsorbent material 20' is in powder form.

In use, the superabsorbent material 20' forms a stable gel upon absorption of a fluid, e.g. water.

The at least one component separated from a fluid 15' is permanently removed from the fluid 15' and/or retained by the superabsorbent 20'.

The support material 21' impregnated with the superabsorbent material 20' comprises a cellulosic material or a polyester material, e.g. a cellulose tissue material or a polyester fibre material.

In this embodiment, the polyacrylate superabsorbent material impregnated in a cellulosic fibrous material is in the form of a Brightwake wound dressing.

The superabsorbent material 20' and/or the support material 21' may further comprise additives.

Conveniently, the superabsorbent material 20' and/or the support material 21' are impregnated with stabilising agents, e.g. anti-microbial agents, to further stabilise the waste product for safe disposal.

The device 1' is provided with attaching means or holes 50' for attaching the device 1' to a static piece of surgical equipment, e.g. a stand or a bed, or to agitation means.

In this embodiment, the device 1' is a bodily fluid separation device, e.g. a blood separation device.

In use, a subject's bodily fluid may provided into the receiving portion 30' of the separation device 1', while the device 1' is provided on or attached to a static piece of surgical equipment such as a stand or a bed. When a desired amount of bodily fluid 15' is provided in the separation device 1', the inlet 25' is closed or sealed to prevent leakage, and the device 1' is transferred to agitation means to improve separation efficiency.

Alternatively, the separation device 1' may be provided on or in said agitation means prior to its receiving portion 30' being filled with a subject's bodily fluid 15'. By such provision agitation may be applied either simultaneous or subsequent to a subject's bodily fluid 15' being provided into the receiving portion 30' of the device 1'.

Figure 3:
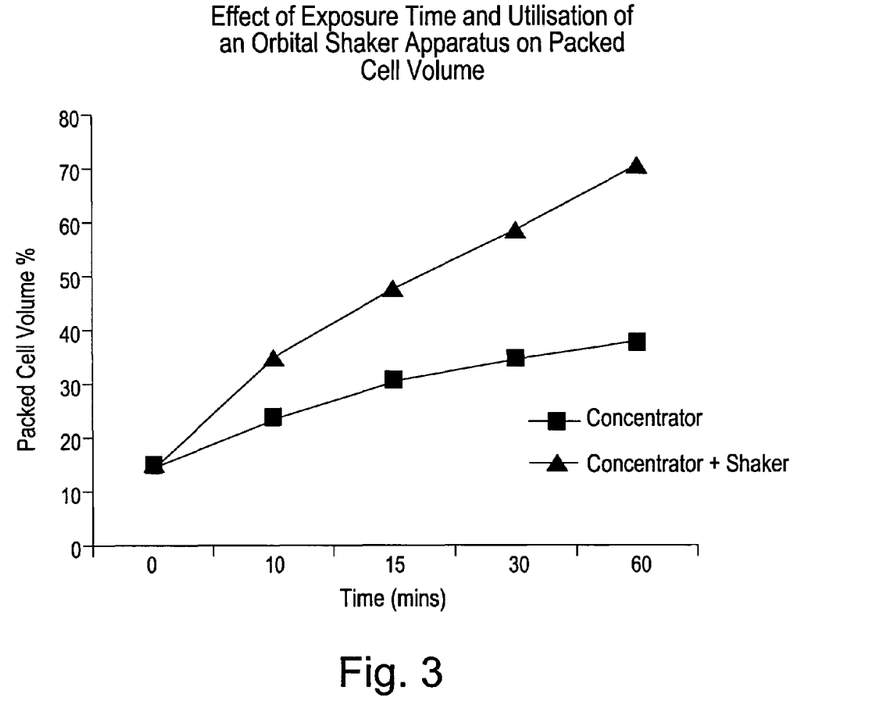
FIG. 3 a graph representing the effect of agitation (using an orbital shaker) on the efficiency of the separation device of FIG. 2(a), when the processed fluid is blood.

FIG. 3 shows the effect of agitation on the efficiency of a separation device according to the second embodiment of the present invention, when the processed fluid is blood. FIG. 3 illustrates the significant enhancement of the efficiency of the separation device when an orbital shaker is used in combination with the separation device. For example, FIG. 3 shows approximately a 2-fold increase in packed cell volume concentration after 30 minutes when an orbital shaker is used. It is believed that agitation prevents the larger blood particles from covering or aggregating on the surface of the filtration member, e.g. a semi-permeable membrane. Such effect can occur as the filtered component is drawn from the fluid and absorbed by or into the superabsorbent material through the filtration member. Agitation ensures, in use, homogeneous mixing of the fluid to-be-processed, e.g. blood, thus maintaining the efficiency of the filtering member by preventing covering of its surface by larger particles.

It will be appreciated that the embodiments of the invention hereinbefore described are given by way of example only and are not meant to limit the scope thereof in any way.

It will particularly be appreciated that while the fluid processed by the separation device of the disclosed embodiments consists of blood, the invention may be applied to process other fluids, e.g. other types of bodily fluids.

The invention claimed is:

1. An apparatus for processing blood into a blood cell concentrate, the apparatus comprising:
   a permeable membrane defining, within it, an inner compartment, wherein the permeable membrane has an effective pore size of 0.2-8 μm and is capable of allowing water, salts, and proteins to pass through the permeable membrane;
   a container comprising a substantially transparent portion, the container surrounding the permeable membrane and the inner compartment, the container defining an outer compartment between the permeable membrane and the container into which blood is initially received;
   an inlet in the container for introducing blood into the outer compartment of the container;
   an outlet in the outer compartment of the container distant from the inlet; and
   a valve or seal on the inlet and the outlet which permits and prevents selective entry and discharge of material to and from the outer compartment of the container and has a flow control system to prevent blood flow from escaping from the container; and a superabsorbent material surrounded by the permeable membrane, wherein the superabsorbent material expands as the superabsorbent material absorbs water, salts, and proteins removed from the blood which have passed through the permeable membrane, thereby leaving a blood cell concentrate in the outer compartment.

2. The apparatus of claim 1, wherein the apparatus is capable of reducing the volume of the blood by at least 20%.

3. The apparatus of claim 1, wherein the superabsorbent material is impregnated in a support material.

4. The apparatus of claim 3, wherein the support material impregnated with the superabsorbent material comprises a cellulosic material or a polyester material.

5. The apparatus of claim 1, wherein the container is in the form of a flexible pouch.

6. The apparatus of claim 1, wherein the permeable membrane is made from a polymeric material.

7. The apparatus of claim 1, wherein the superabsorbent material is made from a superabsorbent polymer.

8. A system for processing blood into a blood cell concentrate comprising:
the apparatus of claim 1 and
an agitation means.

9. The system of claim 8, wherein the agitation means comprises an orbital shaker.

10. A method for processing blood into a blood cell concentrate comprising:
providing the apparatus of claim 1;
introducing blood, containing water, salts, and proteins, via the inlet, into the container;
passing the water, salts, and proteins through the permeable membrane into the inner compartment and leaving a blood cell concentrate in the outer compartment;
absorbing the water, salts, and proteins in the superabsorbent material; and
recovering the blood cell concentrate from the outer compartment via the outlet.

11. The method of claim 10 further comprising:
agitating the apparatus.

12. The apparatus of claim 1, wherein the superabsorbent material precludes the requirement of external force to separate the water, salts, and proteins to be moved from the blood.

13. The apparatus of claim 1, wherein the inlet comprises a means for feeding fluid into the container.

14. The apparatus of claim 1, wherein the permeable membrane defines the shape and size of the container.

15. The apparatus of claim 1, wherein the transparent portion comprises a vertical strip.

16. The apparatus of claim 1, wherein the transparent portion comprises a means to measure the volume of blood in the apparatus.

17. The apparatus of claim 1, wherein the superabsorbent material forms a stable gel upon absorption of the water, salts, and proteins removed from the blood.

18. The apparatus of claim 1 further comprising:
a covering portion.

19. The apparatus of claim 1 further comprising:
a further processing means.

20. The apparatus of claim 19, wherein the further processing means is a filter.

21. The method of claim 10, wherein the flow control system provides a controlled rate at which the blood escapes from the container.

* * * * *